(12) United States Patent
Fang et al.

(10) Patent No.: US 9,765,026 B2
(45) Date of Patent: Sep. 19, 2017

(54) FORMS OF APREMILAST AND THE PROCESS OF MAKING THE SAME

(71) Applicant: ScinoPharm Taiwan, Ltd., Tainan (TW)

(72) Inventors: Hsiao-ping Fang, Tainan (TW); Wei-Shuo Lo, Tainan (TW); Kuan Hsun Wang, Tainan (TW); Yu-Sheng Lin, Kaohsiung (TW); Tsung-Cheng Hu, Tainan (TW); YuanChang Huang, Kaohsiung (TW)

(73) Assignee: SCINOPHARM TAIWAN, LTD., Tainan (CN)

( * ) Notice: Subject to any disclaimer, the term of this patent is extended or adjusted under 35 U.S.C. 154(b) by 0 days.

(21) Appl. No.: 15/246,392

(22) Filed: Aug. 24, 2016

(65) Prior Publication Data

US 2017/0057916 A1    Mar. 2, 2017

Related U.S. Application Data

(60) Provisional application No. 62/211,280, filed on Aug. 28, 2015, provisional application No. 62/279,147, filed on Jan. 15, 2016.

(51) Int. Cl.
*C07D 209/50* (2006.01)
*C07D 209/48* (2006.01)

(52) U.S. Cl.
CPC ......... *C07D 209/50* (2013.01); *C07D 209/48* (2013.01); *C07B 2200/07* (2013.01); *C07B 2200/13* (2013.01)

(58) Field of Classification Search
None
See application file for complete search history.

(56) References Cited

U.S. PATENT DOCUMENTS

| 6,962,940 | B2 | 11/2005 | Muller et al. |
| 7,893,101 | B2 | 2/2011 | Muller et al. |
| 8,093,283 | B2 | 1/2012 | Muller et al. |
| 8,952,178 | B2 | 2/2015 | Zhang et al. |
| 2014/0081032 | A1 | 3/2014 | Connolly et al. |
| 2015/0283249 | A1 | 10/2015 | Khera et al. |

FOREIGN PATENT DOCUMENTS

| CN | 104447445 A | 3/2015 |
| EP | 2730278 A1 | 5/2014 |
| WO | WO-2009/120167 A1 | 10/2009 |
| WO | WO-2016/189486 A1 | 12/2016 |

OTHER PUBLICATIONS

International Search Report mailed on Jan. 13, 2017, for PCT Application No. PCT/SG2016/050413, filed Aug. 25, 2016, 4 pages.
Written Opinion mailed on Jan. 13, 2017, for PCT Application No. PCT/SG2016/050413, filed Aug. 25, 2016, 11 pages.

*Primary Examiner* — Samantha Shterengarts
(74) *Attorney, Agent, or Firm* — Mintz, Levin, Cohn, Ferris, Glovsky and Popeo, P.C.

(57) ABSTRACT

The present invention provides novel crystalline forms of apremilast hemitoluene solvate, apremilast hydrate, and apremilast anhydrate and an amorphous form of apremilast, and processes for the preparation of these forms.

8 Claims, 10 Drawing Sheets

Figure 1: An X-ray powder diffraction pattern for crystalline Form I of apremilast.
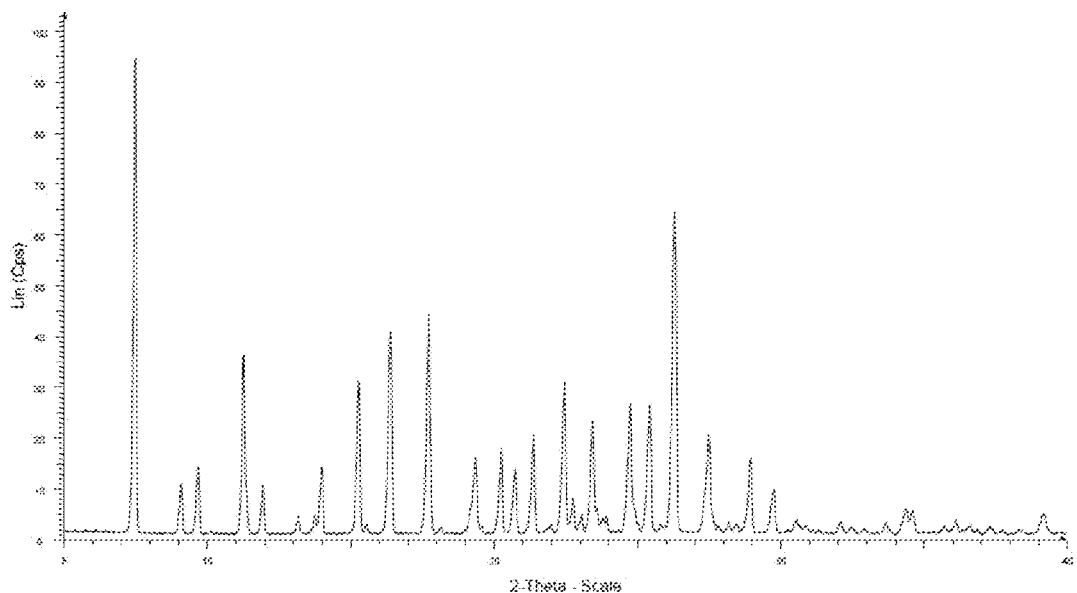
Figure 2. The overlay of TGA and DSC thermograms for crystalline Form I of apremilast
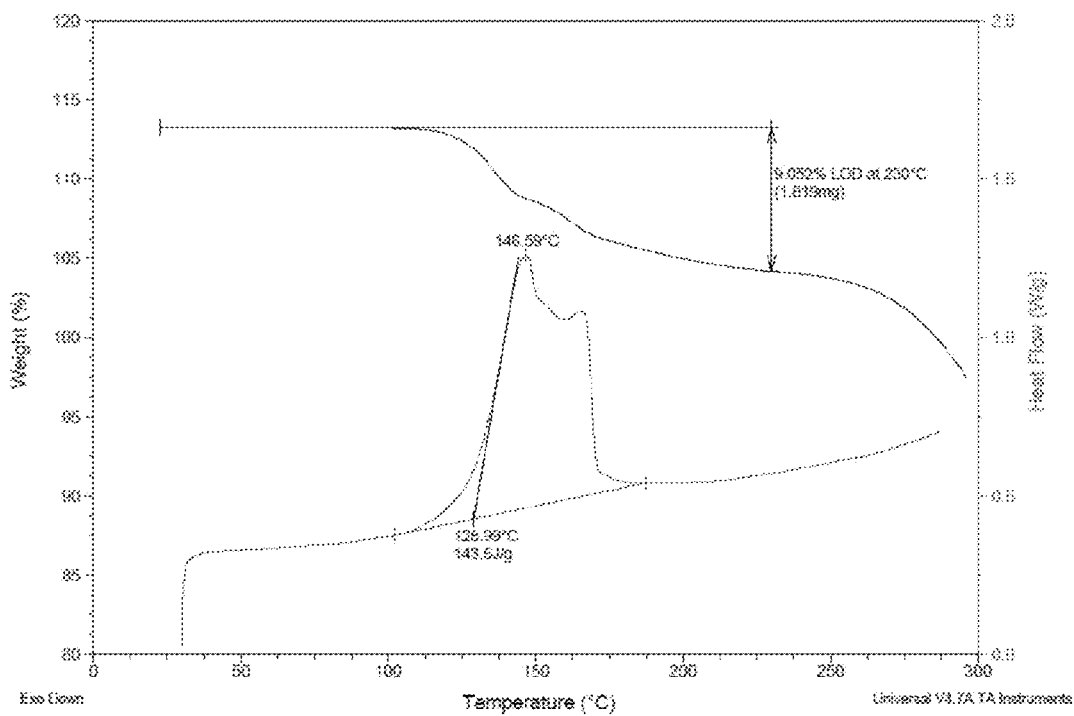

Figure 3: An X-ray powder diffraction pattern for crystalline Form II of apremilast
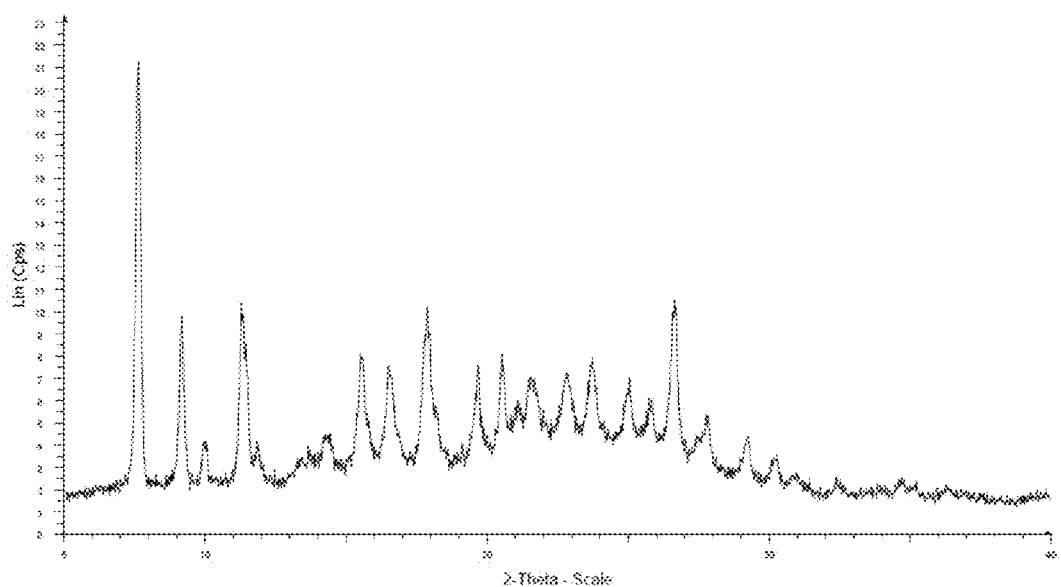
Figure 4. The overlay of TGA and DSC thermograms for crystalline Form II of apremilast
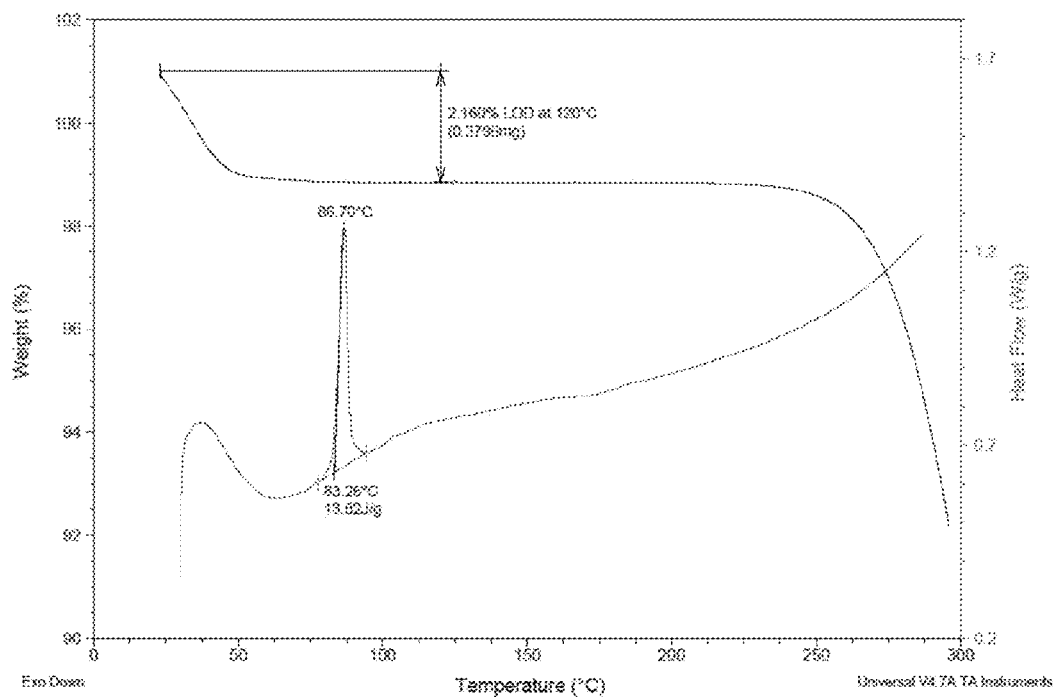

Figure 5A: Dynamic Vapor Sorption plots for Form II of apremilast
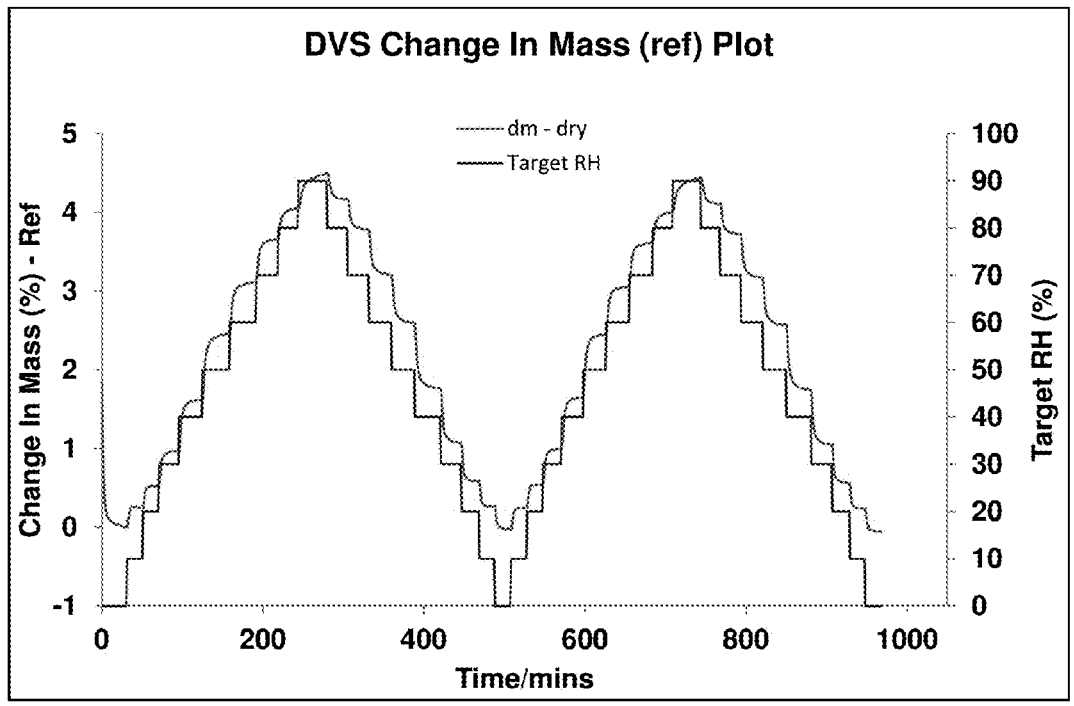
Figure 5B: Dynamic Vapor Sorption plots for Form II of apremilast
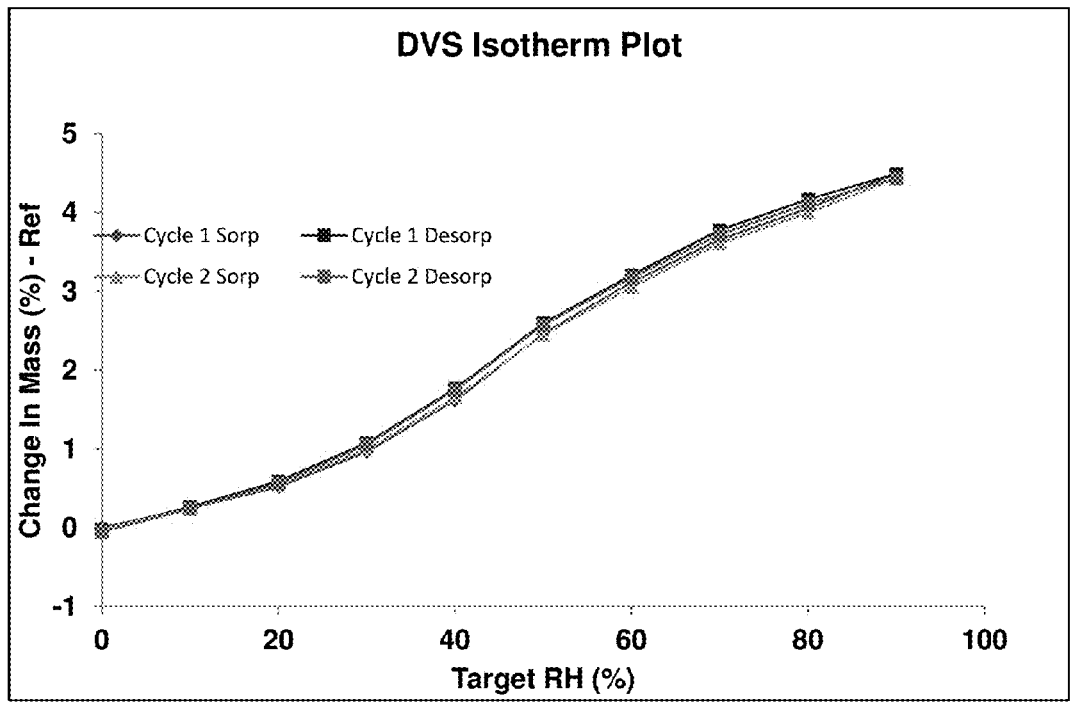

Figure 6: An X-ray powder diffraction pattern for crystalline Form 3 of apremilast
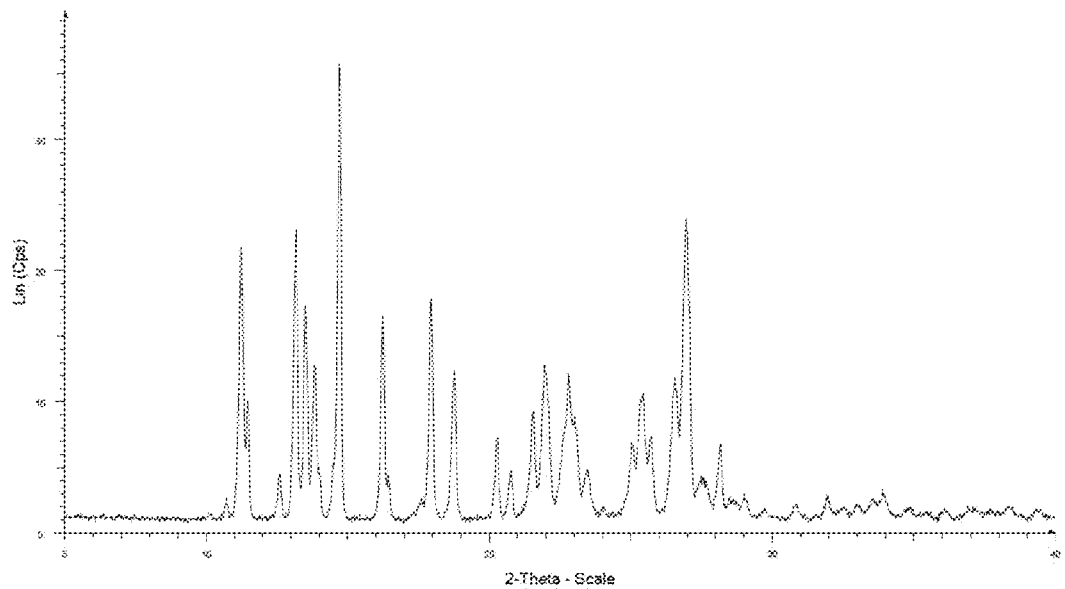
Figure 7: The TGA thermograms for crystalline Form 3 of apremilast
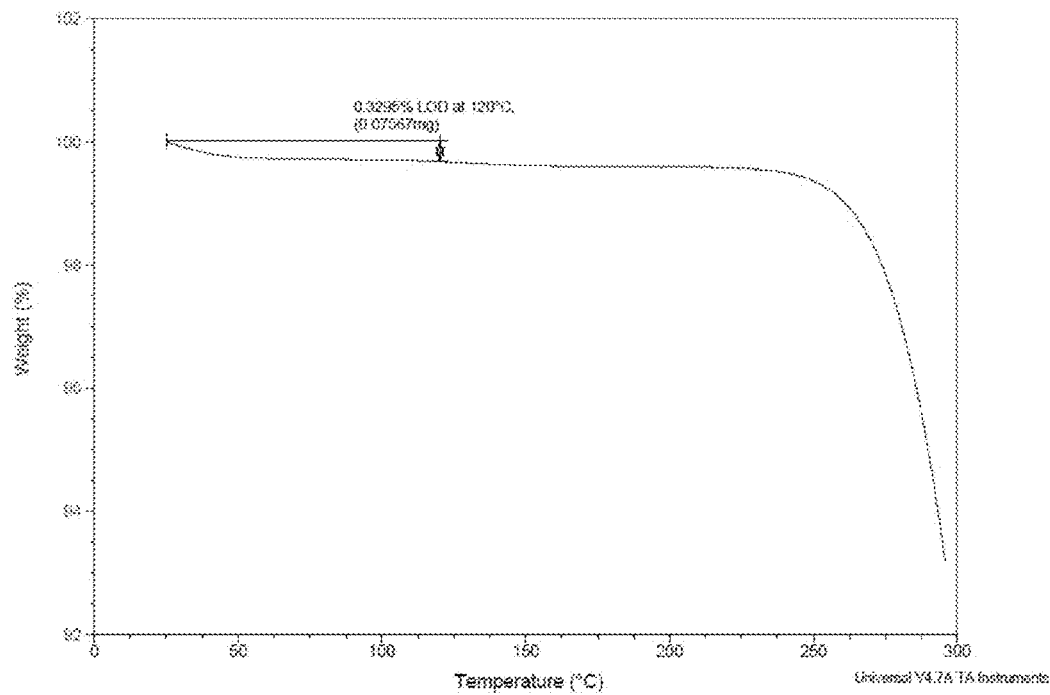

Figure 8: The DSC thermograms for crystalline Form 3 of apremilast
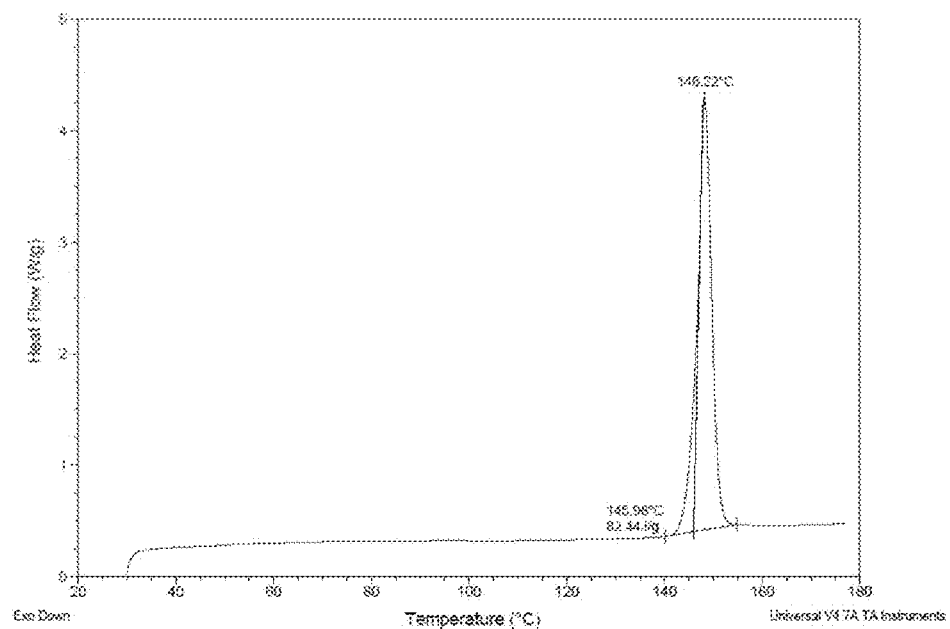

Figure 9: An X-ray powder diffraction pattern for Form 4 of apremilast characterized by X-ray powder diffractometer.
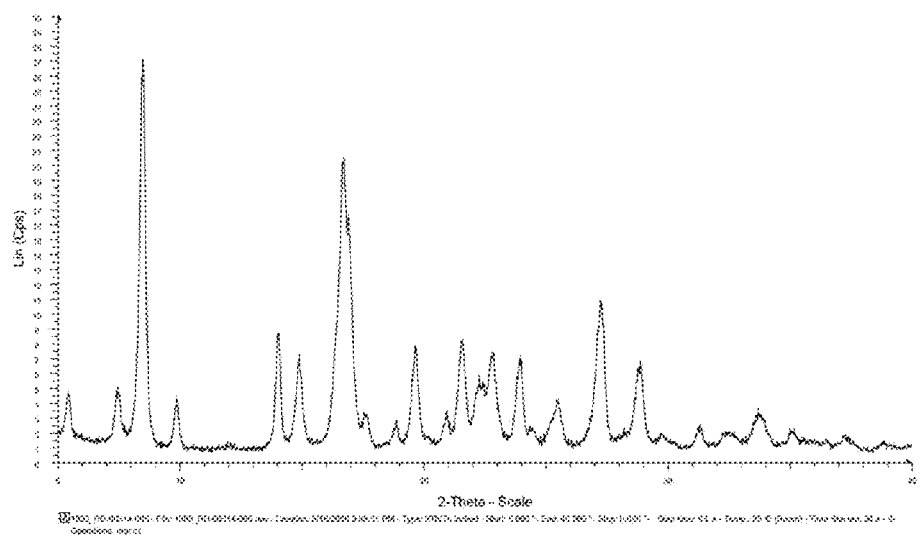

Figure 10: The TGA thermograms for crystalline Form 4 of apremilast.
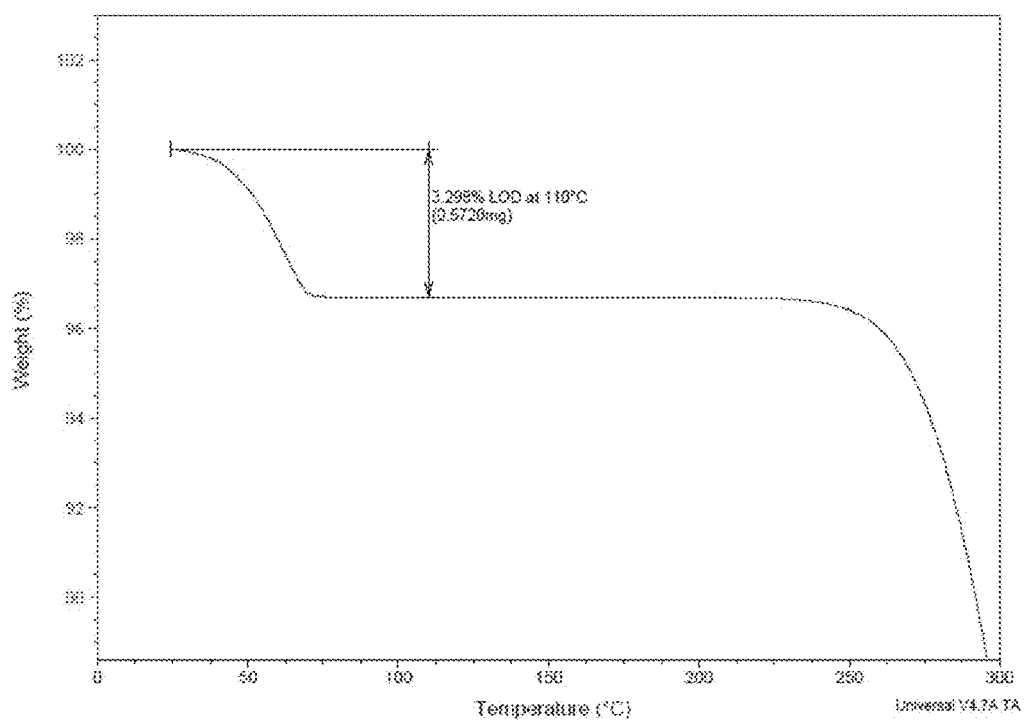

Figure 11: The DSC thermograms for crystalline Form 4 of apremilast.
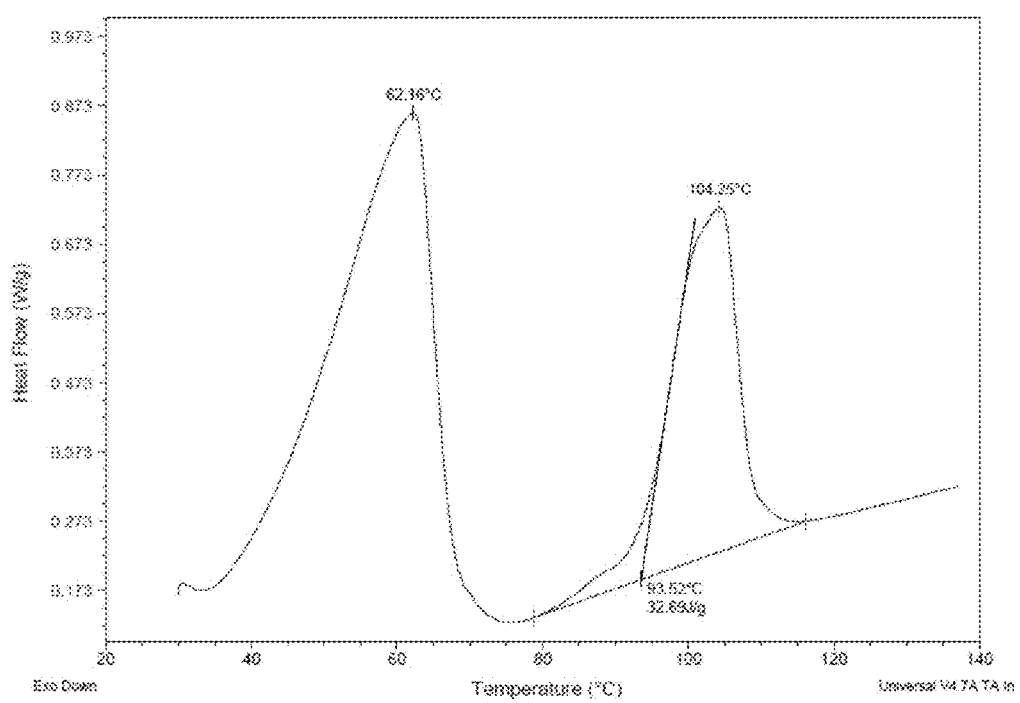

Figure 12: The DVS isotherm for crystalline Form 4 of apremilast hydrate.
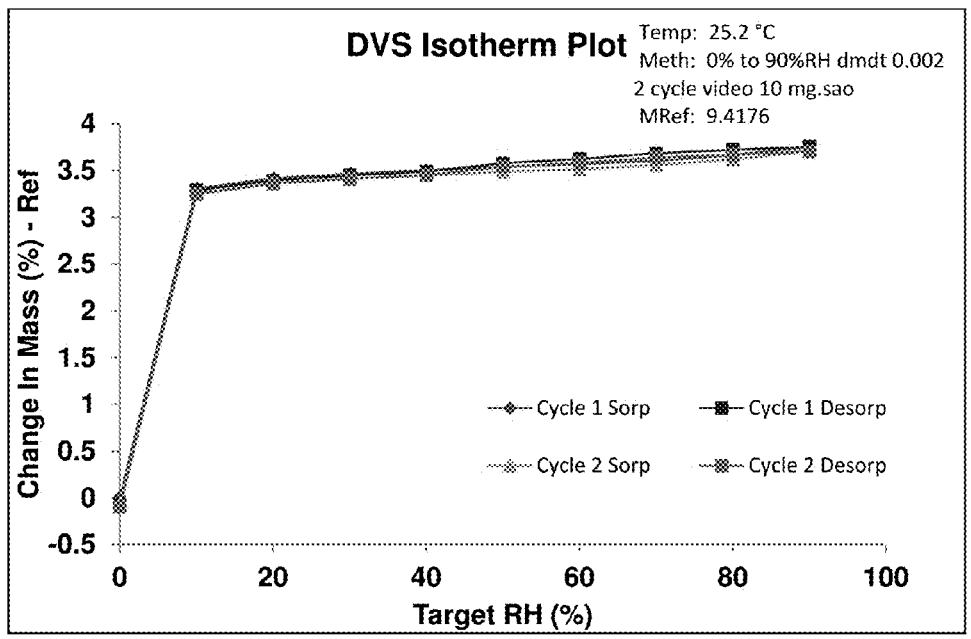
Figure 13: An X-ray powder diffraction pattern for amorphous of apremilast characterized by X-ray powder diffractometer.
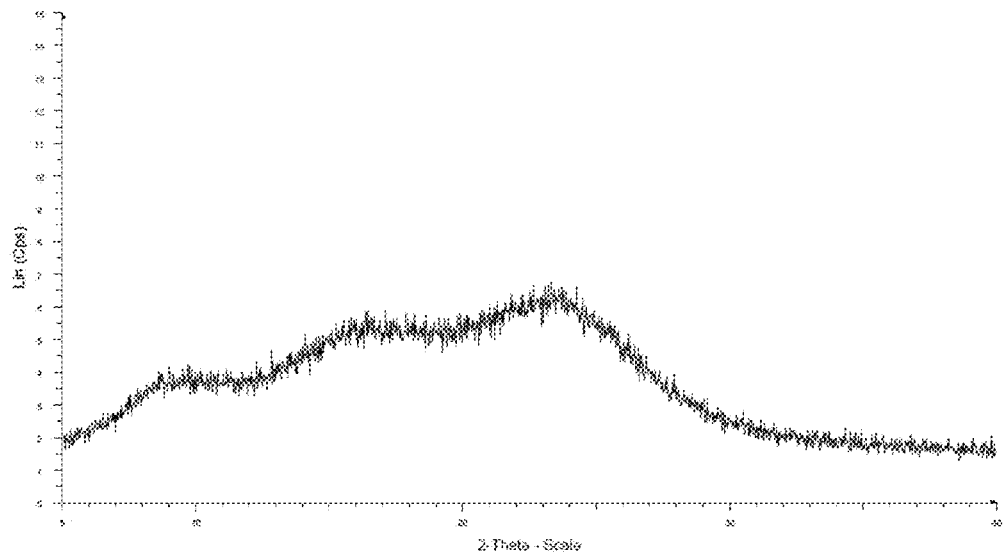

Figure 14: The overlay of TGA and DSC thermograms for amorphous of apremilast
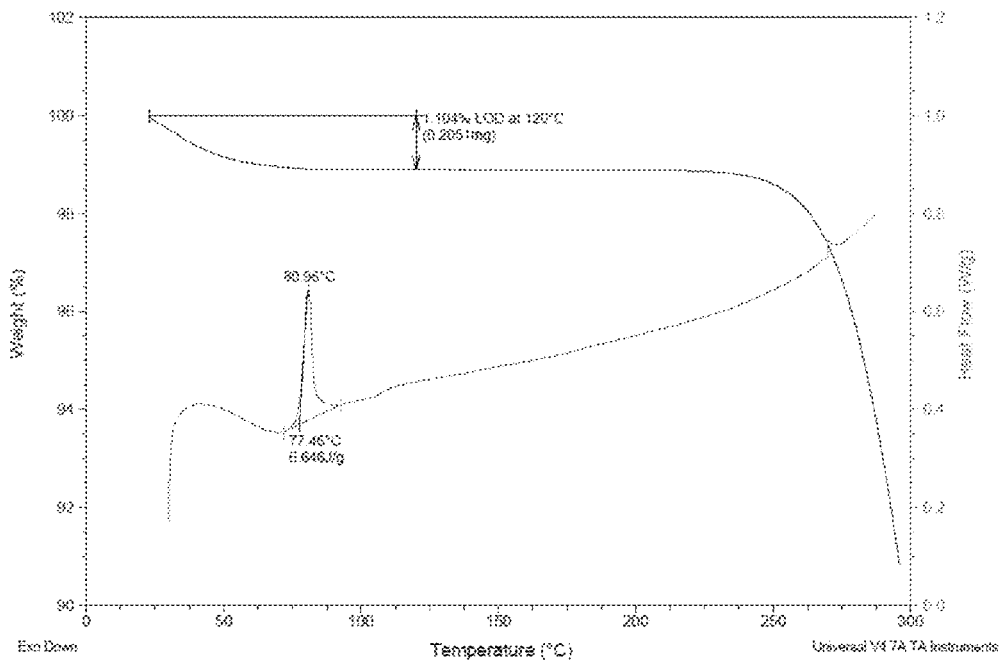
Figure 15: The DVS isotherm for amorphous of apremilast
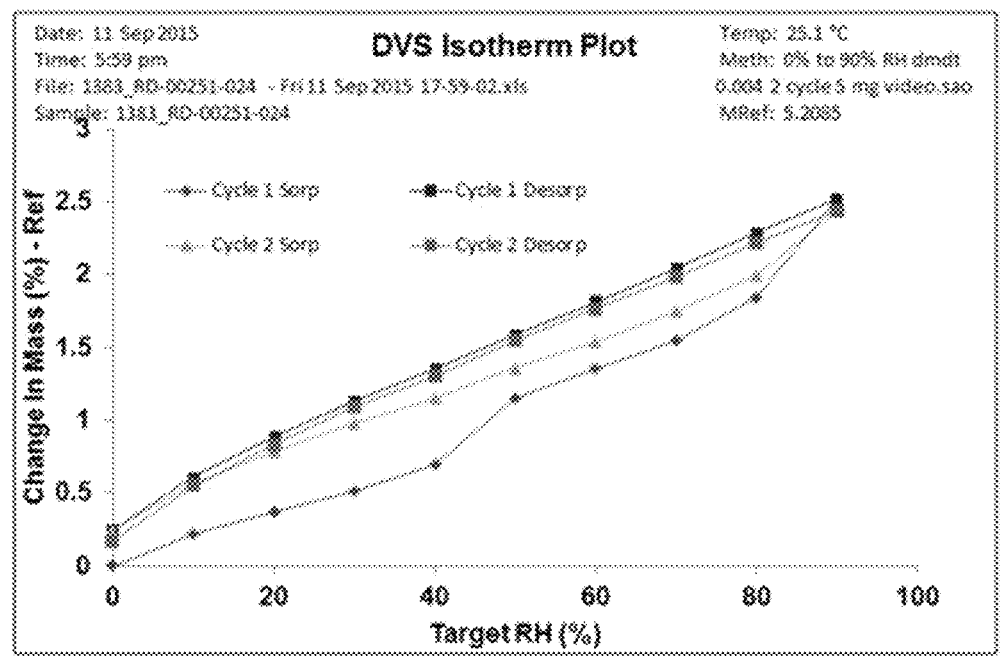

FORMS OF APREMILAST AND THE PROCESS OF MAKING THE SAME

CROSS-REFERENCES TO RELATED APPLICATIONS

This application claims the benefit of priority under 35 U.S.C. §119(e) to U.S. Provisional Application Ser. No. 62/211,280 filed on Aug. 28, 2015 and U.S. Provisional Application Ser. No. 62/279,147 filed on Jan. 15, 2016, the disclosures of each being incorporated herein by reference in their entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Apremilast is a phosphodiesterase 4 (PDE4) inhibitor indicated for the treatment of (1) adult patients with active psoriatic arthritis, and (2) patients with moderate to severe plaque psoriasis who are candidates for phototherapy or systemic therapy.

In U.S. Pat. No. 6,962,940 B2, Muller et al. disclosed that apremilast was produced by heating (S)-1-(3-ethoxy-4-methoxyphenyl)-2-(methylsulfonyl)ethanamine N-Ac-L-Leucine salt 1 with 3-acetamidophthalic anhydride 2 in HOAc (acetic acid) at reflux temperature (~118° C.) overnight (Scheme 1).

Scheme 1: Preparation of Apremilast (U.S. Pat. No. 6,962,940 B2)

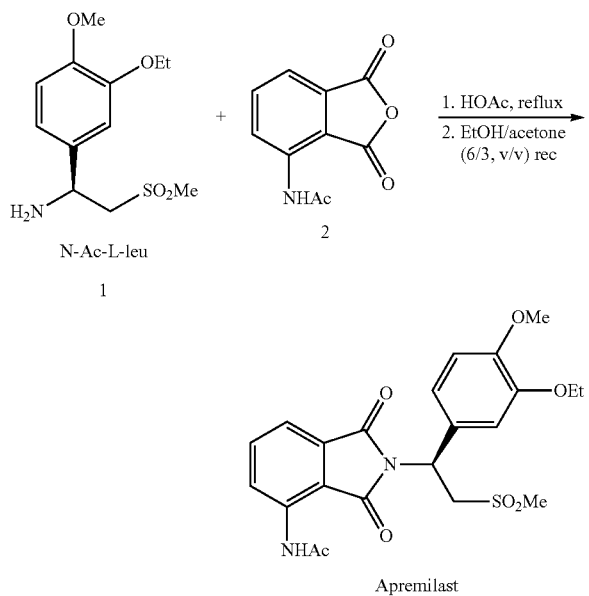

Most of the HOAc was removed by distillation under reduced pressure, and EtOAc was added to the concentrate achieving a homogeneous solution. The solution was successively washed with $H_2O$ (twice), saturated $NaHCO_{3(aq)}$ (twice), saturated $NaCl_{(aq)}$ (twice) and then dried over $Na_2SO_4$. The mixture was filtered, and most of EtOAc was removed by distillation under reduced pressure affording crude apremilast. After recrystallization from a mixture of acetone/EtOH, purified apremilast was obtained in 75% yield with 98% ee. Information of purity and the polymorph for the resulting apremilast was not reported.

A closely related example was disclosed in US 20140081032 A1 where $d_3$-(S)-aminosulfone N-Ac-L-Leucine salt $d_3$-1 was first neutralized to give its corresponding $d_3$-(S)-aminosulfone without further purification. The $d_3$-(S)-aminosulfone was used directly for apremilast formation (Scheme 2).

Scheme 2: Preparation of $d_3$-Apremilast in U2014081032A1

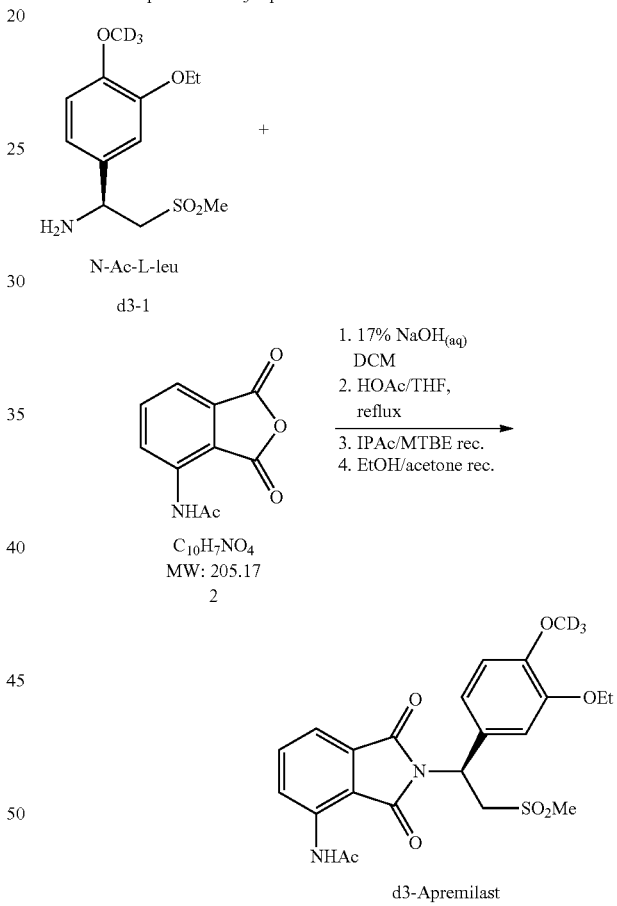

A mixture containing $d_3$-(S)-aminosulfone and 3-acetamidophthalic anhydride 2 was heated in a mixture of HOAc/THF at reflux temperature (~70° C.) for 24 hr. The mixture was diluted with THF and IPAc after reaction completion. The resulting mixture was sequentially washed with 10% $NaH_2PO_{4(aq)}$ (three times) and $H_2O$ (three times). The washed mixture was concentrated under reduced pressure affording crude $d_3$-apremilast. After successive recrystallization from a mixture of IPAc/MTBE and a mixture of acetone/EtOH, purified $d_3$-apremilast was obtained in 79% yield with 99.9% purity and 99.0% ee. Information regarding the polymorph for the resulting apremilast was not available.

In U.S. Pat. Nos. 7,893,101 B2 and 8,093,283 B2, Celgene Corporation disclosed several polymorphs of apremilast including Forms A, B, C, D, E, F and G.

BRIEF SUMMARY OF THE INVENTION

The present invention provides a method for the preparation of apremilast, as well as novel crystalline forms of apremilast hemitoluene solvate, anhydrate and hydrate. Amorphous forms of apremilast are also provided. Processes for the preparation of these crystalline and amorphous forms are also provided. The crystalline forms of apremilast hemitoluene solvate, anhydrate, and hydrate are designated as Forms I and II, Form 3 and Form 4.

The above mentioned amorphous and crystalline forms have been characterized by XRPD (X-ray powder diffraction) analysis, TGA (thermogravimetric analysis) analysis and DSC (differential scanning calorimetry) analysis.

In comparison with the preparative processes disclosed in the art, the reaction in the present disclosure is conducted in HOAc/toluene at lower temperature (90° C. as compared to 118° C.) and crude apremilast is precipitated during cooling without any solvent replacement and aqueous workup. That is, a lower reaction temperature is used and tedious solvent replacement and aqueous workup are not required. The apremilast obtained directly from the precipitation is the crystalline form of apremilast hemitoluene (Form I).

In comparison with the form F disclosed in U.S. Pat. No. 8,093,293, Form 3 and Form 4 in the present disclosure needs less process time to be prepared and is stable even at 40° C./75% RH for 4 weeks.

BRIEF DESCRIPTION OF THE DRAWINGS

FIG. 1 provides an XRPD pattern for a crystalline form of apremilast hemitoluene solvate (Form I), characterized by X-ray powder diffractometer with peaks at about 7.4, 9.0, 9.6, 11.2, 11.9, 13.1, 13.9, 15.3, 16.3, 17.7, 19.3, 20.2, 20.7, 21.3, 22.4, 23.4, 24.7, 25.4, 26.3, 27.5, 28.9, 29.8, 34.4, 34.6 and 39.2±0.2 degree two-theta.

FIG. 2 provides the TGA and DSC thermograms of a crystalline form of apremilast hemitoluene solvate (Form I).

FIG. 3 provides an XRPD pattern for a crystalline form of apremilast anhydrate (Form II), characterized by X-ray powder diffractometer with peaks at about 7.6, 9.1, 10.0, 11.3, 14.3, 15.5, 16.5, 17.9, 19.7, 20.5, 21.5, 22.8, 23.7, 25.0, 25.8, 26.6, 27.8, 29.2 and 30.2±0.2 degree two-theta.

FIG. 4 provides the TGA and DSC thermograms of a crystalline form of apremilast anhydrate (Form II).

FIGS. 5A-5B provide Dynamic Vapor Sorption plots of a crystalline form of apremilast anhydrate (Form II).

FIG. 6 provides an XRPD pattern for a crystalline form of apremilast anhydrate (Form 3), characterized by X-ray powder diffractometer with peaks at about 10.7, 11.2, 11.5, 12.6, 13.1, 13.5, 13.8, 14.7, 16.2, 17.9, 18.7, 20.3, 20.7, 21.5, 22.0, 22.8, 23.5, 25.1, 25.4, 25.7, 26.6, 27.0, 27.5 and 28.2±0.2 degree two-theta.

FIG. 7 provides the TGA thermograms for crystalline Form 3 of apremilast.

FIG. 8 provides the DSC thermograms for crystalline Form 3 of apremilast.

FIG. 9 provides an XRPD pattern for a crystalline form of apremilast hydrate (Form 4).

FIG. 10 provides the TGA thermograms for crystalline Form 4 of apremilast.

FIG. 11 provides the DSC thermograms for crystalline Form 4 of apremilast.

FIG. 12 provides the DVS isotherm for crystalline Form 4 of apremilast.

FIG. 13 provides an XRPD pattern for an amorphous form of apremilast.

FIG. 14 provides the TGA and DSC thermograms of an amorphous form of apremilast.

FIG. 15 provides the DVS isotherm of an amorphous form of apremilast.

DETAILED DESCRIPTION OF THE INVENTION

A concise process for preparing apremilast has now been developed as shown in Scheme 3. (S)-1-(3-ethoxy-4-methoxyphenyl)-2-(methylsulfonyl)ethanamine 3 (>99.9% ee) and 3-acetamidophthalic anhydride 2 were heated in toluene in the presence of HOAc at elevated temperature until the reaction was completed.

Scheme 3: A New Preparation of Apremilast Form I

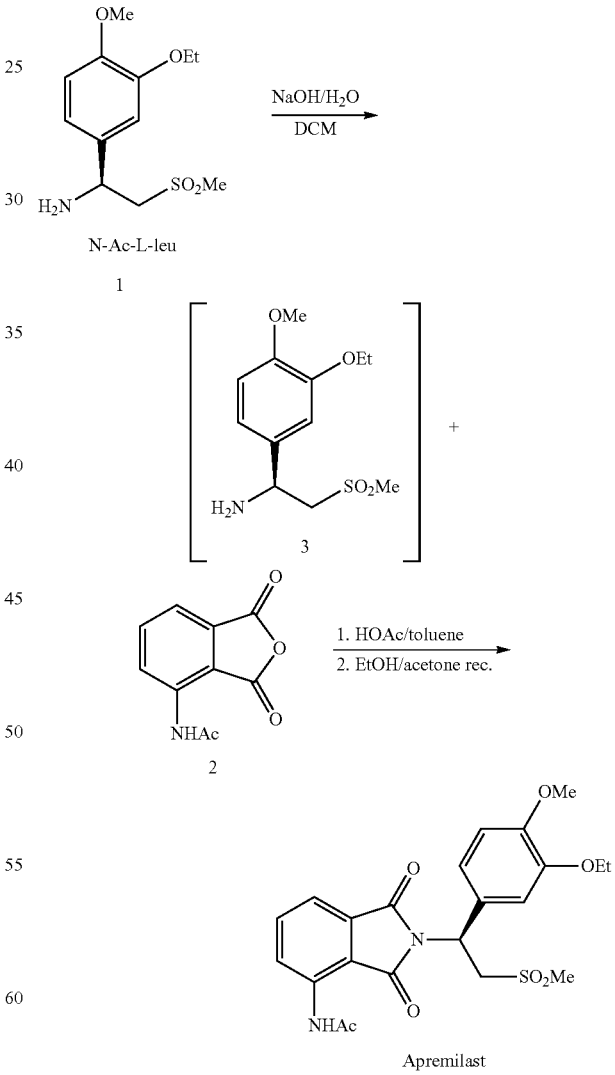

Also provided herein are crystalline forms of apremilast hemitoluene solvate, hydrate and anhydrate and amorphous forms of apremilast. The above-mentioned crystalline forms and amorphous forms can be produced by the methods described herein, and in some embodiments, are substantially free of other crystalline forms. The term "substantially free" refers to an amount of 10% or less of another form, preferably 8%, 5%, 4%, 3%, 2%, 1%, 0.5%, or less of another form.

EMBODIMENTS OF THE INVENTION

Preparation of Apremilast

In one aspect, provided herein is a method of preparing apremilast (essentially as shown in Scheme 3 above) in which (S)-1-(3-ethoxy-4-methoxyphenyl)-2-(methylsulfonyl)ethanamine 3 (>99.9% ee) and 3-acetamidophthalic anhydride 2 are heated in toluene in the presence of HOAc at elevated temperature until the reaction was completed. Upon cooling, apremilast can be collected from the mixture by filtration.

More specifically, (S)-1-(3-ethoxy-4-methoxyphenyl)-2-(methylsulfonyl)ethanamine 3 (>99.9% ee) in toluene can be combined with HOAc and 3-acetamidophthalic anhydride 2, and heated at about 90° C. for about 3 hr to complete the reaction. Apremilast solids precipitate from the mixture with cooling to 20-30° C. Further cooling of the mixture to about 0-10° C. and stirring for about 30 min to about 2 hr, or for about 1 hr provides apremilast hemitoluene solvate. The solid apremilast hemitoluene solvate is preferably collected by filtering and can be obtained in >90% yield with >99.5% purity and >99.5% ee, and in some embodiments can be obtained in 91% yield with 99.94% purity and >99.9% ee. In some embodiments, the apremilast that is obtained is isolated as apremilast hemitoluene solvate (Form I).

Concisely, the process for preparing apremilast comprises:
 a) contacting (S)-1-(3-ethoxy-4-methoxyphenyl)-2-(methylsulfonyl)ethanamine and 3-acetamidophthalic anhydride in toluene and HOAc at elevated temperature to form a mixture; and
 a) isolating apremilast from the mixture of step a).

In some embodiments, the elevated temperature is from 80-100° C., and in other embodiments, the elevated temperature is about 90° C. As noted above, the apremilast that is isolated is typically apremilast hemitoluene solvate.

In some embodiments, the isolating of step b) comprises filtering the mixture of step a).

The ratio of toluene to HOAc (v/v) is generally from about 5/1 to about 15/1, more specifically a ratio of about 7.5/1 (v/v) can be used.

Crystalline Form of Apremilast Hemitoluene Solvate (Form I)

In another embodiment, a crystalline form of apremilast hemitoluene solvate (hereinafter referred as Form I) is provided and has been characterized by a X-ray powder diffraction ("XRPD") pattern with peaks at about 7.4, 9.0, 9.6, 11.2, 11.9, 13.1, 13.9, 15.3, 16.3, 17.7, 19.3, 20.2, 20.7, 21.3, 22.4, 23.4, 24.7, 25.4, 26.3, 27.5, 28.9, 29.8, 34.4, 34.6 and 39.2±0.2 degrees two-theta (2θ). Form I is also characterized by a powder X-ray diffraction pattern as substantially depicted in FIG. 1. In some embodiments, the crystalline form of apremilast hemitoluene solvate (Form I) is characterized by at least 5 peaks, at least 7 peaks, at least 9 peaks, or at least 11 peaks from the list provided above and having peak intensities substantially as provided in FIG. 1.

Form I is further characterized by a weight loss of about 9% at a temperature up to 230° C., as measured by thermal gravimetric analysis ("TGA"). The TGA trace is shown in FIG. 2.

Form I is still further characterized by a DSC plot comprising an endothermic event at the range over 100° C.-190° C. The DSC trace is shown in FIG. 2.

The process for preparing Form I comprises:
 a) heating of 3-acetamidophthalic anhydride and (S)-1-(3-ethoxy-4-methoxyphenyl)-2-(methylsulfonyl)ethanamine in toluene in the presence of acetic acid until the reaction is completed;
 b) cooling the mixture to afford a slurry;
 c) filtering and drying the solids to give apremilast in Form I.

Crystalline Form of Apremilast Anhydrate (Form II)

In another embodiment, a crystalline form of apremilast anhydrate (hereinafter referred as Form II) was characterized by XRPD pattern with peaks at about 7.6, 9.1, 10.0, 11.3, 14.3, 15.5, 16.5, 17.9, 19.7, 20.5, 21.5, 22.8, 23.7, 25.0, 25.8, 26.6, 27.8, 29.2 and 30.2±0.2 degrees two-theta (2θ). Form II is also characterized by a powder X-ray diffraction pattern as substantially depicted in FIG. 3. In some embodiments, the crystalline form of apremilast anhydrate (Form II) is characterized by at least 5 peaks, at least 7 peaks, at least 9 peaks, or at least 11 peaks from the list provided above and having peak intensities substantially as provided in FIG. 3.

The TGA trace of Form II is shown in FIG. 4. As shown in FIG. 4, there is a weight loss of about 2.2% at a temperature up to 120° C. The weight loss is due to the water absorbed on the surface of Form II. This is further supported by Dynamic Vapor Sorption (DVS) plots show in FIGS. 5A and 5B. Referring to FIG. 5A, the water content of Form II not only increases as the relative humidity (RH) in the environment increases but also decreases as RH decreases. Referring to FIG. 5B, when RH is 90%, the water content is as high as 4.5%. However, the water can be removed under 40° C. in the vacuum. In view of above, Form II is hygroscopic.

Form II is further characterized by a DSC plot comprising an endothermic event with an onset temperature of about 83.3° C. The DSC trace is shown in FIG. 4.

The process for preparing Form II comprises:
 a) heating apremilast in acetonitrile to achieve a homogeneous solution;
 b) cooling the homogeneous solution to afford a slurry; and
 c) filtering and drying the solids at 35-55° C. to give apremilast in Form II.

Crystalline Apremilast Anhydrate (Form 3)

In another embodiment, a novel crystalline form of apremilast anhydrate (hereinafter referred to as Form 3) is provided, which is characterized by a powder X-ray diffraction ("XRPD") pattern with peaks at about 10.7, 11.2, 11.5, 12.6, 13.1, 13.5, 13.8, 14.7, 16.2, 17.9, 18.7, 20.3, 20.7, 21.5, 22.0, 22.8, 23.5, 25.1, 25.4, 25.7, 26.6, 27.0, 27.5 and 28.2±0.2 degrees two-theta (2θ). Form 3 is also characterized by a powder X-ray diffraction pattern with peaks at about 11.2, 11.5, 13.1, 13.5, 13.8, 14.7, 16.2, 17.9, 18.7, 20.3, 21.5, 22.0, 22.8, 25.1, 25.4, 25.7, 26.6, 27.0 and 28.2±0.2 degrees two-theta (2θ). Form 3 is preferably characterized by a powder X-ray diffraction pattern substantially as depicted in FIG. 6.

Form 3 is further characterized by a weight loss of about 0.33% at a temperature up to 120° C., as measured by thermal gravimetric analysis ("TGA"). The TGA trace is shown in FIG. 7.

Form 3 is still further characterized by a DSC plot comprising an endothermic event at the range over 140° C.-155° C. The DSC trace is shown in FIG. 8.

The process for preparing the crystalline Form 3 of apremilast comprises
  a) heating apremilast in acetone to produce a homogeneous solution;
  b) combining the homogeneous solution with water at 0-10° C. to form a suspension; and
  c) warming the suspension to obtain the crystalline Form 3 of apremilast.

In some embodiments, the process for preparing the crystalline Form 3 of apremilast further comprises
  d) filtering the suspension of step c) to form a wet cake; and
  e) drying the wet cake to produce the isolated crystalline Form 3 of apremilast.

In some embodiments, the ratio of acetone/water (v/v) in step b) ranges from about 1/4.5 to 1/12, from about 1/4 to 1/10 or from about 1/8 to 1/10. In some embodiments, the ratio of acetone/water (v/v) is about 5/42.5. In some embodiments, the ratio of acetone/water is about 1/9.

In some embodiments, the temperature of step b) is performed at a temperatures ranging from −5-15° C. In some embodiments, the temperature of step b) is performed at a temperatures ranging from 0-10° C. In some embodiments, the temperature of step b) is about 5° C.

In some embodiments, the temperature of warming ranges from about 20 to 30° C. In some embodiments, the temperature of warming is about 25° C.

Crystalline Apremilast Hydrate (Form 4)

In another embodiment, a novel crystalline form of apremilast hydrate (hereinafter referred to as Form 4) is provided, which is characterized by a powder X-ray diffraction ("XRPD") pattern with peaks at about 5.4, 7.4, 8.4, 9.8, 12.0, 14.0, 14.9, 16.3, 16.6, 16.9, 17.6, 18.8, 19.6, 20.9, 21.5, 22.3, 22.8, 23.9, 24.4, 25.2, 25.5, 27.2 and 28.8±0.2 degrees two-theta (2θ). Form 4 is also characterized by a powder X-ray diffraction pattern with peaks at about 5.4, 7.4, 8.4, 9.8, 12.0, 14.0, 14.9, 16.3, 16.6, 16.9, 17.6, 18.8, 19.6, 20.9, 21.5, 22.3, 22.8, 23.9, 24.4, 25.2, 25.5, 27.2 and 28.8±0.2 degrees two-theta (2θ). Form 4 is preferably characterized by a powder X-ray diffraction pattern substantially as depicted in FIG. 9.

Form 4 is further characterized by a weight loss of about 3.298% at a temperature up to 110° C., as measured by thermal gravimetric analysis ("TGA"). The TGA trace is shown in FIG. 10.

Form 4 is still further characterized by a DSC plot comprising two endothermic events with maximum temperature points at 62.16° C. and 104.25° C. The DSC trace is shown in FIG. 11.

Form 4 is further characterized by hygroscopicity. Dynamic vapor sorption (DVS) analysis of moisture uptake and moisture release as a function of relative humidity (RH) were obtained upon cycling between 0% and 90% RH. It was found that about 3.3% of weigh gained immediately at 10% RH indicating Form 4 is hydrate material. In addition, no significant change in sample weight was obtained when the humidity was increased from 10% to 90% RH and the result showed that Form 4 is non-hygroscopic (see FIG. 12).

The process for preparing the crystalline Form 4 of apremilast comprises
  a) heating apremilast in acetone to produce a homogenous solution;
  b) combining the homogenous solution with water at 0-10° C. to form a suspension;
  c) filtering the suspension to obtain a filter cake;
  d) adding the filter cake to a MeOH/H₂O co-solution at 0-30° C. to form a second suspension;
  e) stirring the second suspension at 0-30° C. for more than 5 hours; and
  f) filtering the second suspension to obtain the crystalline Form 4 of apremilast.

In some embodiments the stirring step e) is performed at 0-10° C. for more than 5 hours. In some embodiments, the stirring step e) is performed at about 25° C. for more than 48 hours.

In some embodiments, step f) in the process for preparing the crystalline Form 4 of apremilast further comprises
  f-i) filtering the second suspension of step e) to form a wet cake; and
  f-iii) drying the wet cake to produce the isolated crystalline Form 4 of apremilast.

In some embodiments, the process for prepairing the crystalline Form 4 of apremilast further comprises
  f-ii) washing the wet cake with methanol/water, wherein step f-ii) occurs prior to step f-iii).

In some embodiments, the process further comprises
  a-i) filtering the solution of step a) to produce a filtrate, wherein step a-i) occurs prior to step b).

Step b) then comprises combining the filtrate with water at 0-10° C. to form a suspension.

In some embodiments, the ratio of acetone/water (v/v) in step b) ranges from about 1/3 to 1/12, from about 1/4 to 1/10 or about 1/5.

In some embodiments, the temperature of step b) is performed at a temperatures ranging from −5-15° C. In some embodiments, the temperature of step b) is performed at a temperatures ranging from 0-10° C. In some embodiments, the temperature of step b) is about 5° C.

In some embodiments, the suspension of step b) is warmed and stirred overnight (e.g., 7-24 hours). In some embodiments, the suspension of step b) is warmed to a temperature of from about 20 to 30° C., and stirred for 7-18 hours. In some embodiments, the suspension of step b) is warmed to a temperature of about 25° C., and stirred for about 10-16 hours.

Amorphous Form of Apremilast

An amorphous form of apremilast is characterized by an XRPD pattern without sharp diffraction peaks. The amorphous form of apremilast is also characterized by an XRPD pattern substantially as depicted in FIG. 13.

The amorphous form of apremilast is further characterized by a weight loss of about 1.1% at a temperature up to 120° C., as measured by thermal gravimetric analysis ("TGA"). The TGA trace is shown in FIG. 14.

The amorphous form of apremilast is further characterized by a DSC plot comprising an endothermic event with an onset temperature of about 77.5° C. The DSC trace is shown in FIG. 14.

The amorphous form of apremilast is still further characterized by hygroscopicity. Dynamic vapor sorption (DVS) analysis of moisture uptake and moisture release as a function of relative humidity (RH) were obtained upon cycling between 0% and 90% RH. The maximum uptake was about 2.5% of the total mass of the sample, as demonstrated in the representative amorphous DVS isotherm in FIG. 15. In certain embodiments, amorphous apremilast is hygroscopic.

The process for preparing the amorphous form of apremilast comprises:
  a) heating apremilast in a solvent to achieve a homogeneous solution;
  b) combining the homogeneous solution with an antisolvent to form a suspension;
  c) filtering the suspension to form a wet cake; and d) drying the wet cake at 20 to 60° C. give amorphous apremilast.

In some embodiments, the solvent in step a) is acetone, DMSO, or a mixture thereof. In some embodiments, the ratio of apremilast to acetone or DMSO (g/mL) ranges from about 1/3 to 1/14, from about 1/4 to 1/14, or more preferably about 1/5.

In some embodiments, the antisolvent is water.

In some embodiments, the temperature of step b) is performed at a temperatures ranging from 0-25° C. In some embodiments, the temperature of step b) is performed at a temperatures ranging from 0-10° C. In some embodiments, the temperature of step b) is about 5° C.

In some embodiments, the temperature of step c) is performed at a temperatures ranging from 0-25° C. In some embodiments, the temperature of step c) is performed at a temperatures ranging from 0-10° C. In some embodiments, the temperature of step c) is performed at a temperatures ranging from 20-25° C. In some embodiments, the temperature of step c) is about 5° C.

In some embodiments, the ratio of acetone/water or DMSO/water (v/v) can range from about 1/7 to 1/14, from about 1/8 to 1/12, or more preferably is about 1/9. In some embodiments, the ratio of acetone/water or DMSO/water (v/v) is about 2/23.

In still other embodiments, a process is provided for preparing an amorphous form of apremilast comprising:
a) heating apremilast in acetonitrile to achieve a homogeneous solution;
b) cooling the mixture to afford a slurry;
c) filtering the slurry and drying the solids produced at 60-100° C. to provide amorphous apremilast.

An alternative process for preparing an amorphous form of apremilast comprises:
a) dissolving apremilast in dimethyl sulfoxide to achieve a homogeneous solution; and
b) adding the solution from step a) into water to obtain amorphous apremilast.

EXAMPLES

The following examples are provided to further illustrate, but not to limit this invention.

Experimental Methodology

X-ray Powder Diffraction patterns were collected on a Bruker AXS D8 Advance diffractometer using Cu Kα1 radiation (40 kV, 40 mA), θ-2θ goniometer, and divergence of 10 mm slits, a Ge monochromator and LynxEye detector. The representative XRPD pattern was collected under ambient condition.

The details of the scanning parameters are:
Angular range: 5-40°
Step size: 0.02°
Scan speed: 0.6 sec/step Thermal Gravimetric Analysis:

TGA data was collected on a TA instrument Q500TGA. Each sample was loaded onto a pre-tared platinum crucible and the balance and furnace were purged with nitrogen prior to the analysis with a flow rate set as 40±5 and 60±5 mL/min, respectively. The heating process was programmed to start from ambient temperature and stop at 300° C. with a 10° C./min ramp.

Differential Scanning Calorimetry

DSC data was collected on a TA Instrument MDSC Q200. Each sample was loaded onto a hermetic pan with pin-hole in the lid and the analysis was carried out under a constant flow of nitrogen (60 mL/min). The heating process was programmed to start from 30° C. and stop at 290° C. with a 10° C./min ramp.

Dynamic Vapor Sorption (DVS)

The sample was placed into the DVS sample pan and dried under a stream of dry nitrogen at 25° C. (0% RH). The moisture was gradually introduced into the system with a 10% RH increment up to 90% RH and the humidity was then decreased in a similar trend for desorption phase. The sorption and desorption data were collected with equilibration set to dm/dt 0.004%/min for 5 min/step. The minimum and maximum time for each step were set to 10 and 360 min. Two sorption/desorption cycles were performed.

Example 1

Preparation of Form I of Apremilast

A mixture containing (S)-1-(3-ethoxy-4-methoxyphenyl)-2-(methylsulfonyl)ethanamine N-Ac-L-Leu 1 (37.4 g, 83.8 mmole, >99.9% ee) and DCM (374 mL) was neutralized with NaOH$_{(aq)}$ (17%, 37 mL). The separated organic portion was subjected to solvent chase with toluene (747 mL). After HOAc (112 mL) and 3-acetamidophthalic anhydride 2 (18 g, 87.7 mmole, 1.05 equiv) were added, the mixture was heated at 90° C. for 3 hr completing the reaction. Apremilast solids precipitated along with cooling to 20-30° C. The mixture was cooled to 0-10° C. and stirred for 1 hr. The mixture was filtered to give apremilast hemitoluene solvate in 91% yield with 99.94% purity and >99.9% ee.

Example 2

Preparation of Form I of Apremilast

A mixture containing (S)-1-(3-ethoxy-4-methoxyphenyl)-2-(methylsulfonyl)ethanamine N-Ac-L-Leu 1 (4.9 g, 11.0 mmole, >99.9% ee), 3-acetamidophthalic anhydride 2 (2.36 g, 11.5 mmole, 1.05 equiv), HOAc (20 mL) in toluene (147 mL) was heated at 90° C. for 3 hr completing the reaction. Apremilast solids precipitated along with cooling to 20-30° C. The mixture was cooled to 0-10° C. and stirred for 1 hr. The mixture was filtered to give apremilast hemitoluene solvate in 86% yield with 99.97% purity and >99.9% ee containing 3.3% of N-acetyl-L-Leucine.

Example 3

Preparation of Form II of Apremilast

A mixture containing of apremilast (5.04 g) and acetonitrile (10 mL) was heated at 40° C. achieving a homogeneous solution. The solution was filtered and the filtrate was cooled to 25° C. After being stirred for 2 hr, the slurry was filtered and the filter cake was purged with nitrogen for 2 hr producing apremilast (4.37 g) in Form E. Apremilast in Form E was heated at 40° C. under 150 torr in an oven for 111 hr providing apremilast in Form II. In contrast, apremilast in Form E was heated at 100° C. under 150 torr in an oven for 17 hr providing amorphous apremilast.

Example 4

Preparation of Form 3 of Apremilast

Apremilast (5 g) and acetone (60 mL) was heated at 24° C. to achieve a homogeneous solution. The solution was filtered to form a filtrate and the filtrate was added to water (250 mL) at 0-10° C. The resulting solution formed a suspension. The suspension was warmed to 25° C. with magnetic stirring and stirred overnight. The suspension was filtered to obtain a wet cake. The wet cake was dried at 25° C. under nitrogen for 1 hr to provide apremilast Form 3.

Example 5

Preparation of Form 3 of Apremilast

Apremilast (20 g) and acetone (80 mL) was heated at 55° C. to achieve a homogeneous solution. The solution was filtered and washed with about a 20 mL acetone rinse to form a filtrate. The filtrate was added to water (850 mL) at 0-10° C. The resulting solution formed a suspension. Some part of the suspension was filtered to obtain a wet cake. The other part of the suspension was added to wet cake, warmed to about 23° C. and aged for 1 hr to form another suspension. The resulting suspension was filtered to obtain a wet cake. The wet cake was dried at 25° C. under nitrogen to provide apremilast Form 3.

Example 6

Preparation of Form 3 of Apremilast

Apremilast (20 g) and acetone (80 mL) was heated at 55° C. to achieve a homogeneous solution. The solution was filtered and washed with about a 20 mL acetone rinse to form a filtrate. The filtrate was added to water (850 mL) at 0-10° C. The resulting solution formed a suspension. The suspension was warmed to 25° C. with magnetic stirring and stirred for 3 hr. The suspension was filtered to obtain a wet cake. The wet cake was dried 25° C. under nitrogen to provide apremilast Form 3.

Example 7

Preparation of Form 4 of Apremilast 5 g of Form B of apremilast and 20 mL of acetone were added to a suitable reactor. The resulting mixture was stirred at about 55° C. for dissolution followed by filtration and rinsed with acetone (5 mL, 1 vol, 0-10° C.). The filtrate was slowly added to purified process water (PPW, 225 mL, 45 vol) for 0.5 hr with 300 rpm while maintaining the temperature at about 0-10° C. After addition, the mixture was stirred with 300 rpm at 0-10° C. for 1 hr and stirred at room temperature overnight. Afterward, the mixture was filtered and the filter cake was washed with a methanol/water co-solution (25 mL, v/v=1/9, 5 vol). The wet cake was then added to a MeOH/H$_2$O co-solution (25 mL, v/v=1/9, 5 vol) and stirred at 0-10° C. for 5 hr. The resulting slurry was filtered and washed with MeOH/H$_2$O co-solution (25 mL, v/v=1/9, 5 vol). The wet cake was suction dried for 1 hr, and then vacuum dried at about 60° C. for 8 hr to provide 4.03 g of Form 4 of Apremilast.

Example 8

Preparation of an Amorphous Form of Apremilast

A mixture containing apremilast in Form B (5 g) and acetonitrile (10 mL) was heated at 50° C. achieving a homogeneous solution. The solution was filtered and the filtrate was cooled to 25° C. After being stirred for 2 hr, the slurry was filtered and the filter cake was purged with nitrogen for 2 hr producing apremilast (4.28 g) in Form E. Apremilast in Form E was dried at 60° C. under 150 torr in an oven for 65 hr providing amorphous apremilast.

Example 9

Preparation of an Amorphous Form of Apremilast

Apremilast (7.52 g) and dimethyl sulfoxide (45 mL) was mixed to achieve a homogeneous solution. The solution was added to 376 mL of water, and stirred for about 0.5 hr. The resulting suspension was filtered and the solid was washed with about 600 mL of water to obtain a wet cake. The wet cake was dried to obtain amorphous apremilast (6.81 g).

Example 10

Preparation of an Amorphous Form of Apremilast

Apremilast (8.4 g) and acetone (40 mL) was heated at 55° C. to achieve a homogeneous solution. The solution was filtered and washed with about a 10 mL acetone rinse to form a filtrate. The filtrate was added to water (450 mL) at 0-10° C. and stirred for 1 hr at 0-10° C. The resulting solution formed a suspension. The suspension was filtered to obtain a wet cake. The wet cake was dried at 40° C. under nitrogen in an oven for 22 hr, then at 60° C. under nitrogen in an oven for 19 hr to provide amorphous apremilast.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A process for preparing apremilast, said process comprising:
    a) contacting (S)-1-(3-ethoxy-4-methoxyphenyl)-2-(methylsulfonyl)ethanamine and 3-acetamidophthalic anhydride in toluene and acetic acid at elevated temperature to form a mixture; and
    b) isolating apremilast from the mixture of step a).

2. The process of claim 1, wherein said elevated temperature is from 80-100° C.

3. The process of claim 1, wherein said elevated temperature is about 90° C.

4. The process of claim 1, wherein said apremilast is isolated as apremilast hemitoluene solvate.

5. The process of claim 1, wherein said isolating comprises filtering the mixture of step a).

6. The process of claim 1, wherein said toluene and acetic acid are in a ratio of 15/1 to 5/1 (v/v).

7. The process of claim 1, wherein said toluene and acetic acid are in a ratio of about 7.5/1 (v/v).

8. The process of claim 1, wherein said apremilast is isolated in >90% yield with >99.5% purity and >99.5% ee.

* * * * *